United States Patent [19]

Broomhead et al.

[11] Patent Number: 5,493,516
[45] Date of Patent: Feb. 20, 1996

[54] DYNAMICAL SYSTEM ANALYZER

[75] Inventors: David S. Broomhead; Robin Jones; Martin Johnson, all of Worcester, United Kingdom

[73] Assignee: The Secretary of State for Defence in Her Britannic Majesty's Government of the United Kingdom of Great Britain and Northern Ireland, London, England

[21] Appl. No.: 404,098

[22] Filed: Mar. 14, 1995

Related U.S. Application Data

[62] Division of Ser. No. 119,138, Oct. 7, 1993, Pat. No. 5,453,470.

[30] Foreign Application Priority Data

Mar. 22, 1991 [GB] United Kingdom ............... 9106082

[51] Int. Cl.⁶ .................................................. G05B 13/02
[52] U.S. Cl. ........................ 364/553; 364/149; 395/903
[58] Field of Search ................................... 364/148–166, 364/221.2, 221.3, 553, 571.04, 571.05, 916.2, 916.3; 395/10, 20, 21, 902, 903, 906

[56] References Cited

U.S. PATENT DOCUMENTS 5,349,541  9/1994  Alexandro et al. .
5,369,726  11/1994 Krecker et al. ................. 395/2.45
5,396,415  3/1995  Konar et al. ..................... 364/162
5,410,495  4/1995  Ramamurthi .................. 364/511.05

FOREIGN PATENT DOCUMENTS 0329356A  8/1989  European Pat. Off. .

OTHER PUBLICATIONS

Arbez; "A Pattern Recognition System For Ambulatory EEG"; Proceedings Of The 7th Ann. Conf. Of The IEEE/Engineering In Medicine And Biology Society, vol. 2, 9.85; pp. 665–667.
Bourne; "The EGG Analysis System Of The National Cooperative Dialysis Study"; IEEE Transactions On Bio–Medical Electronics, vol. BME2/7, No. 11, Nov. 1980; pp. 657–663.
Van Den Bos; "Model Building And Parameter Estimation As Means For Intelligent Measurement"; Measurements, vol. 6, No. 1, Jan. 1988; pp. 26–28.
Tokarzewski, J.; "Controllability Of Non–Linear Time–Invariant Dynamical Systems—Sufficient Conditions"; 1976, Abstract.

*Primary Examiner*—James P. Trammell
*Assistant Examiner*—Craig Steven Miller
*Attorney, Agent, or Firm*—Nixon & Vanderhye

[57]  ABSTRACT

A dynamical system analyzer (10) incorporates a computer (22) to perform a singular value decomposition of a time series of signals from a nonlinear (possibly chaotic) dynamical system (14). Relatively low-noise singular vectors from the decomposition are loaded into a finite impulse response filter (34). The time series is formed into Takens' vectors each of which is projected onto each of the singular vectors by the filter (34). Each Takens' vector thereby provides the co-ordinates of a respective point on a trajectory of the system (14) in a phase space. A heuristic processor (44) is used to transform delayed co-ordinates by QR decomposition and least squares fitting so that they are fitted to non-delayed co-ordinates. The heuristic processor (44) generates a mathematical model to implement this transformation, which predicts future system states on the basis of respective current states. A trial system is employed to generate like co-ordinates for transforation in the heuristic processor (44). This produces estimates of the trial system's future states predicted from the comparison system's model. Alternatively, divergences between such estimates and actual behavior may be obtained. As a further alternative, mathematical models derived by the analyzer (10) from different dynamical systems may be compared.

3 Claims, 7 Drawing Sheets

Fig. 5(a)
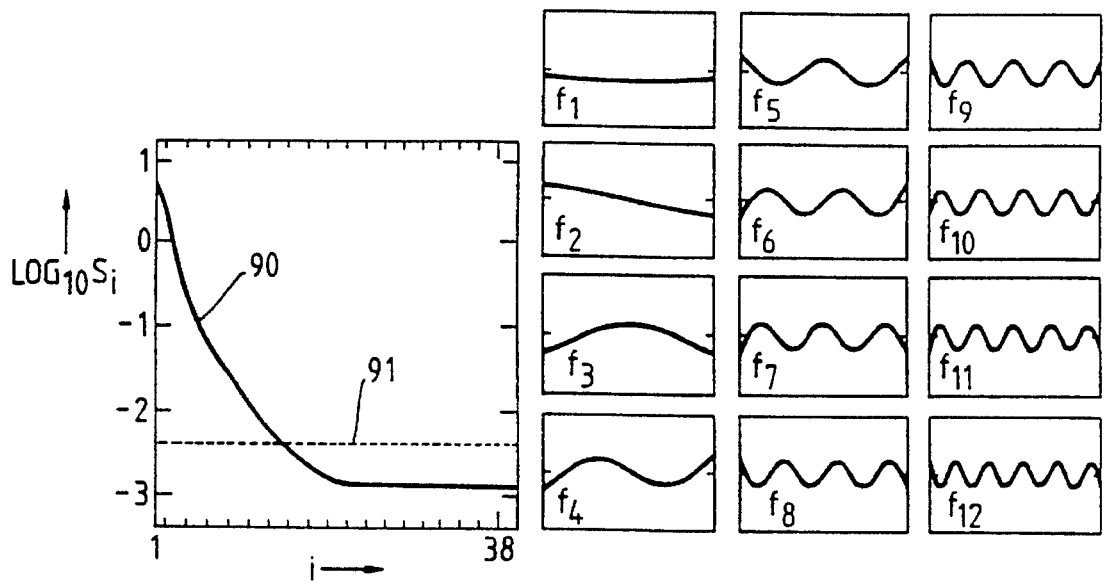
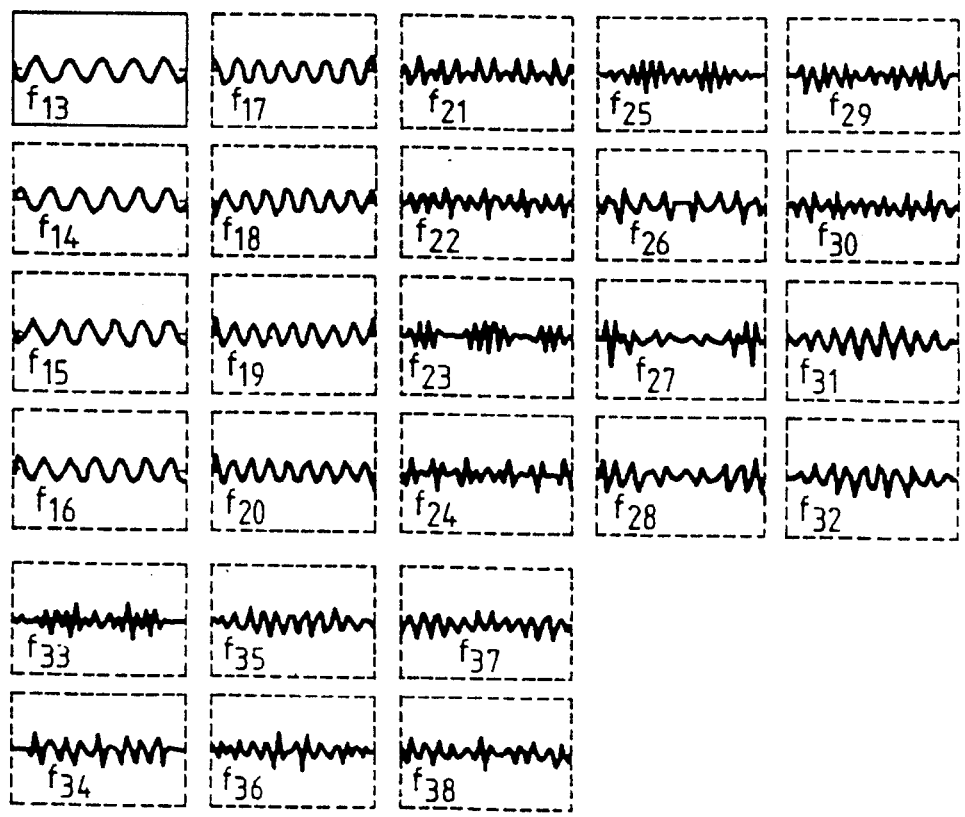
Fig. 5(b)

DYNAMICAL SYSTEM ANALYZER

This is a divisional of application Ser. No. 08/119,138, filed Oct. 7, 1993 U.S. Pat. No. 5,453,490.

This invention relates to a dynamical system analyser, and more particularly to such a device applicable to analysis of dynamical systems which might be nonlinear or chaotic in the mathematical sense.

Investigation of nonlinear dynamical systems presents particular difficulties because traditional electronic spectral analysis tools are not appropriate. As an example, consider a chaotic nonlinear dynamical system arranged to produce an electronic signal characteristic of its behaviour. It is known from dynamical systems research that such a signal can have a substantial continuous component to its spectrum. Filtering in either time or frequency to improve signal to noise ratios can distort or alter the system dynamics as perceived from a filtered signal. This is exemplified by the papers of Badii et al in Phys. Rev. Lett. 60 (1988) p. 979 and Milschske et al. in Phys. Rev. A37 (1988) p. 4518. Moreover, power spectrum analysis is insufficient to characterise the dynamics of a system when data exhibits deterministic chaos resulting in a continuous spectrum (as opposed to a set of harmonics with a simple relationship). This is discussed by F. C. Moon in a work entitled "Chaotic Vibrations", Wiley-Interscience. Spectrally selective signal processing of this kind, intended to simplify analysis, can render the apparent system behaviour more complex.

The behaviour of a dynamical system is commonly represented by a curve in a multi-dimensional phase space. Successive points on the curve indicate the evolution of the system as a function of time. The line is referred to as a "trajectory", and the region of phase space to which it is confined after an arbitrary time is called an "attractor". If the dynamical system is chaotic, the region is called a "strange attractor". The attractor is the phase space region in which the system behaviour is localised, and to which it can be said to be "attracted".

There is a need for a device which is applicable to the analysis of nonlinear systems, since traditional techniques merely complicate the apparent behaviour instead of reducing it to identifiable components. Traditional techniques such as Fourier spectral analysis are applicable only to systems which can be modelled as the linear superposition of a limited number of harmonic modes.

There is a particular need for a device which can detect a change from normal system behaviour to chaotic behaviour. This is of particular importance in the field of aero-engines and other mechanical motive power sources. Such power sources are characterized by highly regular oscillatory and/or rotational behaviour in normal operation, but develop irregular characteristics before failing catastrophically. A device capable of detecting onset of wear-related irregular behaviour would provide a means for anticipating and avoiding catastrophic failure by prior shut-down and repair. It might also provide for reduced servicing costs, since maintenance could be deferred until system behaviour warranted it.

SUMMARY OF THE INVENTION

It is an object of the present invention to provide a dynamical system analyzer.

The present invention provides a dynamical system analyzer characterized in that it includes:

(1) means for generating a sequence of sets of phase space coordinates from a time series of signals from a dynamical system, each coordinate set being projections of a respective Takens' vector on to a set of singular vectors obtained in a singular value decomposition of the said time series of signals or of another such series, and (2) heuristic processing means arranged to carry out a transformation of the said sequence to produce a fit to reference data and to create a mathematical model related to that transformation.

The invention provides the advantage that it produces a mathematical model of a dynamical system, and is applicable to the analysis of non-linear systems. As will be described later, a mathematical model created by the heuristic processing means may be employed to generate predictions of future dynamical system behaviour on the basis of preceding behaviour. Alternatively, mathematical models derived from different dynamical systems may be compared with one another for the purposes of similarity or change analysis.

In a preferred embodiment, the invention provides a dynamical system analyzer including:

(1) means for deriving a time series of signals from a dynamical system, (2) means for generating from the time series a set of singular vectors each associated with a respective singular value which is greater than a noise level of the dynamical system, the set defining a phase space and corresponding to a subset of a set of vectors from a singular value decomposition of the time series, (3) means for transforming the time series into a sequence of sets of phase space co-ordinates, and (4) heuristic processing means arranged to operate in a training mode to carry out a transformation in which the said sequence undergoes QR decomposition (as herein defined) and least squares fitting to reference data in order to generate a mathematical model related to that transformation.

The heuristic processing means may also be arranged to operate in a test mode to transform a further sequence of phase space co-ordinates, and to provide predictive output values on the basis of the mathematical model.

In this embodiment, the invention provides the advantage of being trainable in accordance with reference data to generate a mathematical model. This enables reference data to be selected and also to be replaced if retraining is required.

The heuristic processing means may be arranged to employ in training mode reference data which is either one of or both of the time series and the sequence of sets of phase space co-ordinates derived therefrom. The reference data is input to heuristic processing means with a relative lead time interval over input of the said sequence for QR decomposition and least square fitting; the lead time interval is arranged to be not greater than the inherent predictable timescale of the dynamical system as indicated by its largest Lyapunov component. In this case, the mathematical model which is generated in training mode is that required to extrapolate the phase space trajectory and/or the time series of the dynamical system ahead in time to the extent of the lead time interval. In test mode, the output values correspond to predictions of future behaviour of a trial system which produced the further sequence of phase space co-orinates previously referred to. These values may be the phase space co-orinates and/or the time series of that trial system predicted on the basis of the mathematical model obtained in training mode.

3

Alternatively, or in addition, the heuristic processing means may be arranged to compare the mathematical model's predictions of the trial system's phase space co-orinates and/or time series with actual values of these parameters measured later in time. In this case, error values arise between each prediction and a respective measured parameter. A large error value indicates significant departure from a predicted extrapolation of a phase space trajectory. In a mechanical system, this might be associated with impending catastrophic failure or other unwelcome behaviourial change.

The generating means may be a digital computer programmed to carry out a singular value decomposition of the dynamical system time series. This may be a once and for all computation, in which case its results may be stored in a memory for use when required.

The dynamical system may be a system (such as a mechanical or electronic device) in an initial functionally acceptable state. A trial system to be compared with the dynamical system may be the same system after degradation has occurred in service over a period. This would enable the maintenance requirements of large machines (for example) to be assessed on the basis of behaviourial change.

The transforming means may be a finite impulse response (FIR) filtering device arranged to input the time series in the form of Takens' vectors (as hereinafter defined), and to compute the projections of each Takens' vector on to each of the set of singular vectors obtained by singular value decomposition to provide a respective set of co-ordinates in a phase space for each such Takens' vector.

The heuristic processing means is preferably substantially as described in an International Patent Application No. PCT/GB90/00142 published under the Patent Co-operation Treaty as No. WO 90/09643.

The dynamical system analyzer of the invention may be employed with the heuristic processing means operating in training mode to provide mathematical models of respective dynamical systems. The models may then be compared to provide an indication of the degree of similarity between the systems. Singular vectors obtained from one dynamical system's time series may be employed in the production of phase space coordinates for each of the systems' time series. Alternatively, each system's time series may be used in both singular value decomposition and transformation by the heuristic processing means.

BRIEF DESCRIPTION OF THE DRAWINGS

In order that the invention might be more fully understood, an embodiment thereof will now be described, with reference to the accompanying drawings, in which:

FIGS. 5(a) and 5(b) are equivalent to FIG. 4 except that the relevant system noise level is below digital quantization noise;

4

Figure 6:
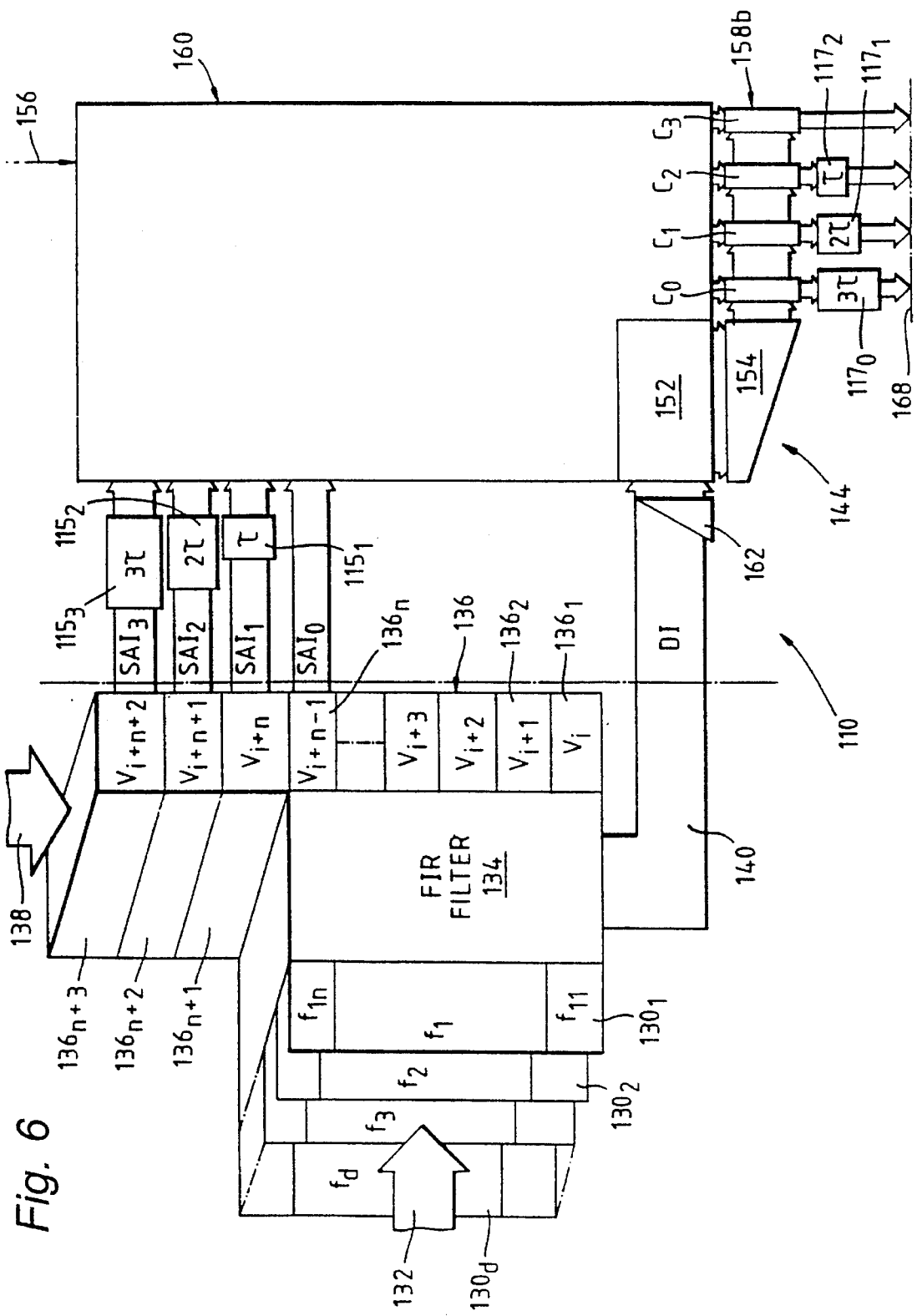
Figure 7:
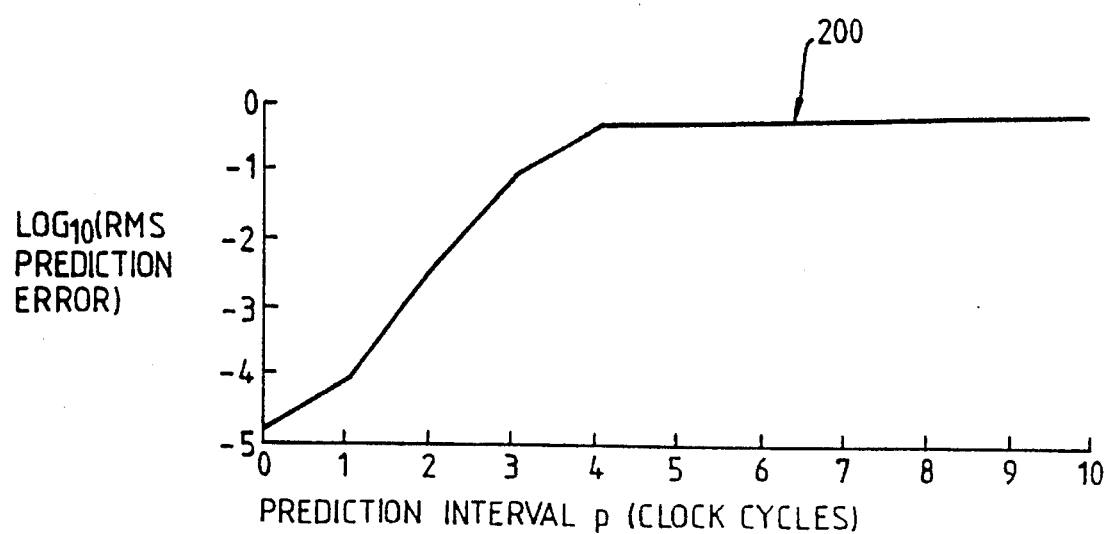

FIG. 6 schematically illustrates an alternative embodiment of the invention arranged for determining system predictability; and FIG. 7 is a graph showing results of the kind which might be obtainable from the FIG. 6 embodiment.

DETAILED DISCUSSION OF PREFERRED EMBODIMENTS

Figure 1A:
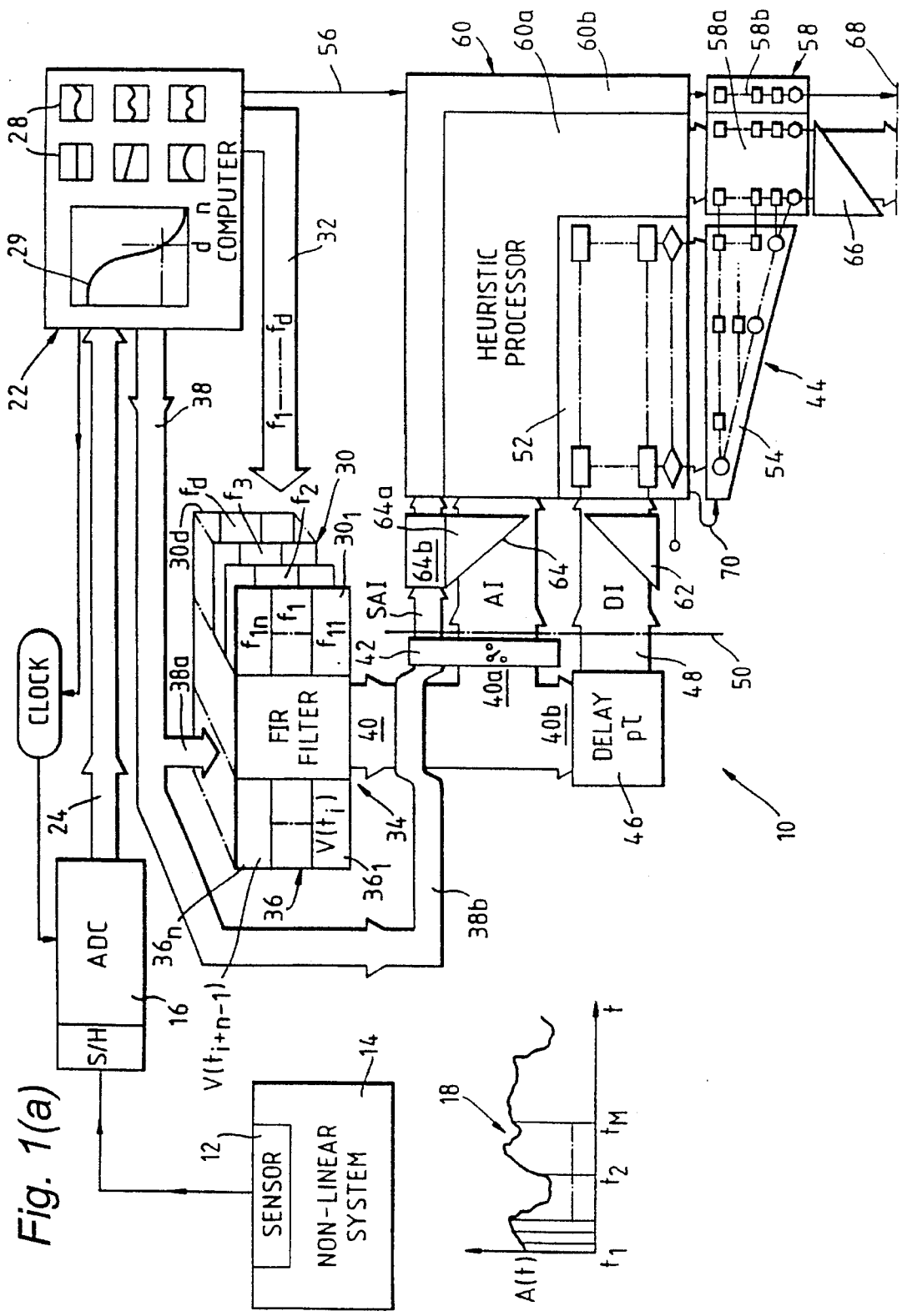
FIG. 1(a) is a schematic block diagram of a dynamical system analyser of the invention in the form of a prediction device.
Figure 1B:
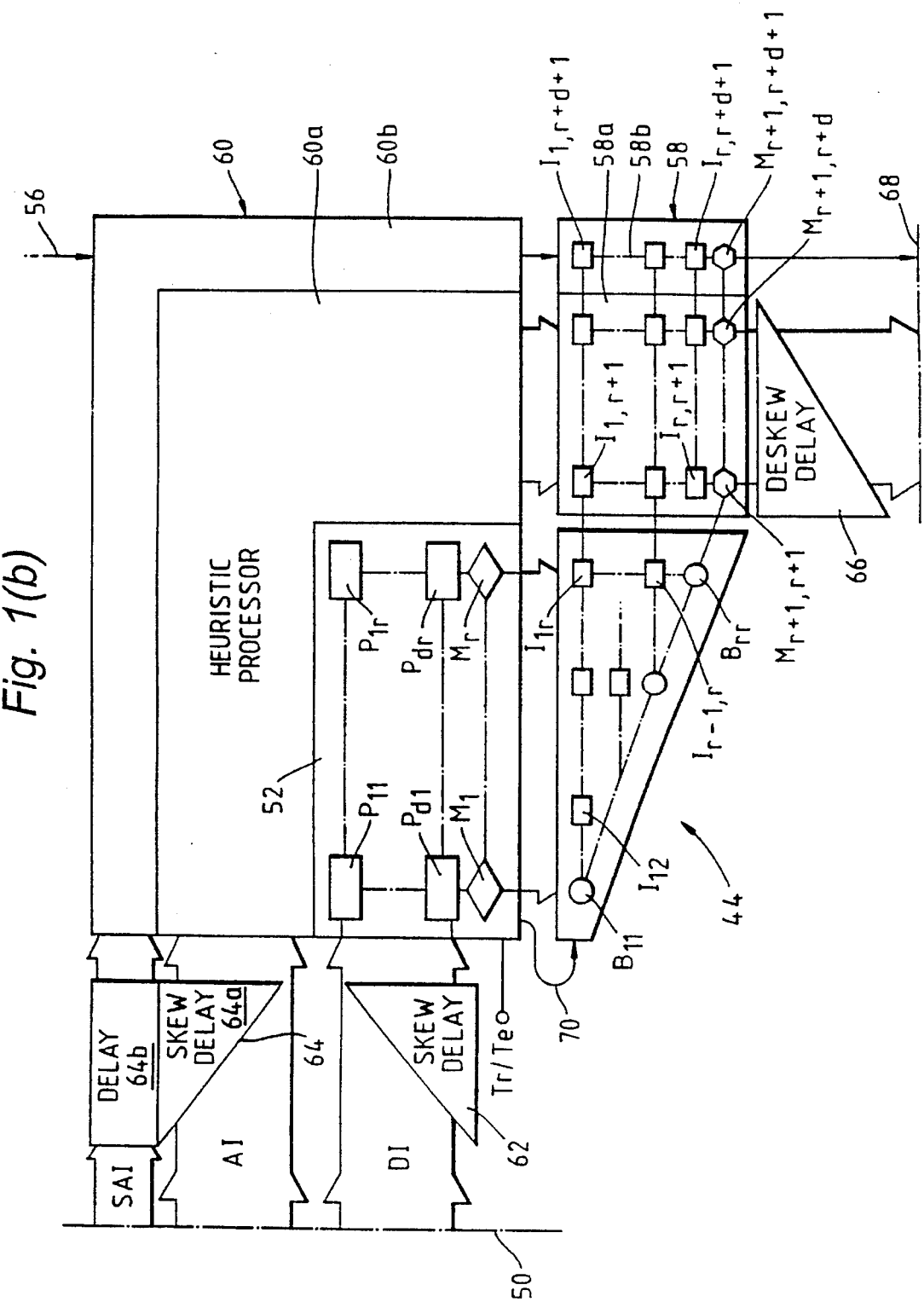
FIG. 1(b) shows a part of FIG. 1(a) in more detail.

Referring to FIGS. 1(a) and 1(b), there is shown a schematic block diagram of a dynamical system analyzer device of the invention device indicated generally by 10.

The device 10 incorporates a sensor transducer 12 mounted on a non-linear system 14 and deriving an analogue electrical signal A(t) characteristic of that system's behaviour. Output signals from the sensor 12 are fed to an analogue to digital converter (ADC) 16. The latter has an input S/H arranged to sample and hold the signal A(t) at successive times $t_1 \ldots t_i \ldots t_M$ with a constant spacing $\tau$. Here $t_i$ is given by:

$$t_i = t_1 + (i-1)\tau \qquad (1)$$

The analogue signal A(t) and sampling times $t_1$ etc are shown in a graph 18. Discrete samples of the signal form a time series $A(t_i)$, where i=1 to M. These are digitized by the ADC 16 to produce a digital time series $V(t_i)$ where $V(t_i)$ corresponds to $A(t_i)$ in each case for i=1 to M.

The ADC 16 operates under the control of a sampling clock 20, which supplied timing pulses at times $\tau$ apart. The magnitude of $\tau$ is set by a computer 22, which supplies a digital word to the clock 20 indicating the required sampling interval.

The digital time series with general term $V(t_i)$ is output from the ADC 16 to the computer 22 in bit-parallel form via a computer input bus 24. The computer 22 stores this time series on a hard disc, and calculates the mean and variance of the time series terms $V(t_i)$ to $V(t_M)$. It produces a normalized version of the time series, and then processes it to provide a singular value decomposition. The decomposition will be described in more detail later. It yields a set of singular vectors $f_1$ to $f_d$, each of which is a mathematical function expressed as a series of n successive values. Some of the vectors are illustrated schematically in boxes such as 28, and their corresponding singular value spectrum is indicated schematically at 29.

The computer 22 loads the singular vectors $f_1$ to $f_d$ into a random access memory (RAM) 30 via a first output bus 32. The RAM 30 has respective portions $30_1$ to $30_d$ for the vectors $f_1$ to $f_d$. Each portion such as $30_1$ stores n values per vector, e.g. $f_{11}$ to $f_{1n}$ for $f_1$. The RAM 30 is incorporated in a multi-dimensional finite impulse response (FIR) filter 34, which also incorporates a chain 36 of n multi-bit delay latches $36_1$ to $36_n$. Parts of the RAM 30 and latch chain 36 which are not illustrated explicitly are indicated by dotted lines. The FIR filter 34 is of generally known and commercially available kind. One such incorporating a RAM 30 and latch chain 36 was offered for sale in May 1985 by Calmes Systems Inc., a Canadian corporation. The FIR filter 34 may alternatively be based on devices as set out in U.S. Pat. Nos. 4,885,715 and 4,833,635 referred to as correlators and convolvers.

The latch chain 36 receives input of the stored digital time series values such as $V(t_i)$ from the computer 22 via a spur 38a of a second output bus 38. The bus 38 also supplies a clock signal to the FIR filter 34. This provides for successive values $V(t_i)$ etc in the digital time series to be clocked into a final latch $36_n$ of the chain 36. Each value is a multibit parallel digital word, and its bits are input synchronously. After input, each time series value is clocked onwards down the chain towards a first latch $36_1$ at the rate of one latch per clock cycle. After n clock cycles, the digital time series portion $V(t_1)$ to $V(t_n)$ is stored on latches $36_1$ to $36_n$ respectively. This is known in electronics as a delay register prefill operation. After prefill, the computer 22 supplies a clock signal actuation to the FIR filter 34 to initiate its filtering operation. The operation of the filter 34 is to multiply each time series value by a respective singular vector horizontally opposite in FIG. 1(a) to form products such as $V(t_i)f_{11}$ through to $V(t_{i+n-1})f_{1n}$. The products formed on each clock cycle are added to provide a respective total for each singular vector.

Defining the first filter clock cycle as that during which the digital time series signal or element $V(t_1)$ became loaded into the FIR filter 34, then the filter outputs on the ith filter clock cycle co-ordinates $g_1(i)$ to $g_d(i)$ given by:

$$g_1(i) = \sum_{j=1}^{n} V(t_{i+j-1})f_{1j} \qquad (2.1)$$

$$g_k(i) = \sum_{j=1}^{n} V(t_{i+j-1})f_{kj} \qquad (2.k)$$

$$g_d(i) = \sum_{j=1}^{n} V(t_{i+j-1})f_{dj} \qquad (2.d)$$

Equations (2.1) to (2.d) indicate that the ith digital time series value $V(t_i)$ is used by the FIR filter 34 to form a set of co-ordinates $g_1(i)$ to $g_d(i)$. These co-ordinates are produced over the time series subset of n successive values $V(t_i)$ to $V(t_{i+n-1})$, and represent the position at time $t_i$ of a vector representing the nonlinear system in a phase space having d dimensions defined by respective basis vectors $f_1$ to $f_d$. The general co-ordinate $g_k(i)$ is the projection of the time series subset $V(t_i)$ to $V(t_{i+n-1})$ on to the general basis vector (singular vector) $f_k$. The subset of n values $V(t_i)$ to $V(t_{i+n-1})$ is referred to as a Takens' vector, after F Takens, "Detecting Strange Attractors in Turbulence", Lecture Notes in Mathematics, Ed. D. A. Rand and L. S. Yound, Springer, Berlin 1981 p. 366. The ith Takens' vector has an lth element $T_l(i)$ defined by:

$$T_l(i) = V(t_{i+l-1}) \qquad (3)$$

Varying the element number l from 1 to n generates $V(t_i)$ to $V(t_{i+n-1})$. The general co-ordinate $g_k(i)$ produced on the ith filter clock cycle may be considered as the correlation of the ith Takens' vector with the sequence of values $f_{k1}$ to $f_{kn}$ of the kth singular vector. Mathematically it is the projection of the ith Takens' vector on to the kth singular vector.

The co-ordinates $g_1(i)$ to $g_d(i)$ are output in parallel and in synchronism from the FIR filter 34 on a filter bus 40. Successive co-ordinate sets $g_1(i+1)$ to $g_d(i+1)$, $g_1(i+2)$ to $g_d(i+2)$ etc. are output on successive clock cycles. The filter bus 40 has a first spur 40a connected to a multipole, double throw switch 42, and thence to an answer input AI of an heuristic processor indicated generally by 44. Here the legend "HEURISTIC PROCESSOR" indicates elements AI, DI and 50 to 68b described below. The throws of the switch 42 connect the answer input AI either to the first bus spur 40a or to a zero signal (not shown). A second spur 40b of the filter bus 40 is connected to a delay unit 46, which delays each of the coefficients $g_1(i)$ to $g_d(i)$ by like time intervals of pτ. Here p is an integer and τ is the length of a clock cycle, so the delay is the same integral number of clock cycles for each of the co-ordinates $g_1(i)$ to $g_d(i)$.

The delay unit 46 is connected by a delay output bus 48 to a data input bus DI of the heuristic processor 44. A second spur 38b of the second computer output bus 38 is connected via the switch 42 to a subsidiary answer input bus SAI of the heuristic processor 44. An input interface of the processor 44 is indicated by a chain line 50.

The heuristic processor 44 is of known kind. A detailed description of its construction and mode of operation is given in International Application No. PCT/GB90/00142 published under the Patent Co-operation Treaty (PCT) on 23 Aug. 1990 with an International Publication No. WO 90/09643. Its features will be discussed briefly.

The heuristic processor 44 includes a digital arithmetic unit 52. The latter incorporates arithmetic circuits $P_{11}$ to $P_{dr}$ shown as rectangles. These are arranged in rows $P_{11}$ to $P_{1r}$, ... $P_{d1}$ to $P_{dr}$ and columns $P_{11}$ to $P_{d1}$, ... $P_{1r}$ to $P_{dr}$. The parameter d is the dimensionality of the co-ordinates $g_1(i)$ etc as before. The parameter r is the number of dimensions of the space into which data input to the unit 52 is transformed. The unit 52 also incorporates memories $M_1$ ... $M_r$ shown as diamonds. These are each disposed to receive output signals from a respective column of arithmetic units, such as $P_{11}$ to $P_{d1}$ for memory $M_1$ for example. Devices of the kind P or M which are not illustrated explicitly are denoted by chain lines.

Output from the digital arithmetic unit passes to a triangular systolic array 54 which is also part of the heuristic processor 44. The triangular array 54 is shown vertically foreshortened for illustrational convenience. It incorporates boundary cells $B_{11}$ to $B_{rr}$ indicated by circles, together with internal cells, $I_{12}$ to $I_{r-1,r}$ indicated by squares. Structure not illustrated explicitly is denoted by chain lines. Each boundary cell (referred to generally as B) of the triangular array 54 is arranged to calculate rotation parameters from data input from above, to update a respective stored matrix element and to output the parameters laterally to the right. Each internal cell (referred to generally as I) of the triangular array 54 is arranged to receive rotation parameters from the left, to apply them to data received from above, to generate an output below, to update a respective stored matrix element, and to pass on the rotation parameters to the right. These functions take place on each clock cycle, the heuristic processor 44 receiving a clock signal from the computer 22 via a line 56. This clock signal is relayed to each element of the heuristic processor 44.

The boundary and internal cells B and I are transputers programmed to carry out arithmetic functions. They are designed to implement a rotation algorithm. A matrix of transformed data is output from the digital arithmetic unit 52 at the rate of one matrix row per clock cycle. This is input to the triangular array 54 at a like rate, and elements of the rows are progressively eliminated by a series of rotations in accordance with the algorithm at the rate of one element per row. The result is that the matrix of transformed data from the unit 52 undergoes rotations which convert it to a triangular matrix. There are a number of rotation algorithms which the triangular matrix 54 array might employ. One such employs pairs of rotation parameters consisting of the sines and cosines of respective rotation angles. The boundary and internal cells B and I store and update matrix elements of the triangular matrix. Other computationally more convenient algorithms produce rotation parameter and stored elements mathematically related to such sines, cosines and matrix elements. In particular, in one algorithm, the boundary cells B store a matrix of a first kind and the internal cells I store a matrix of a second kind intended for multiplying the first kind matrix to generate the triangular matrix.

The process of triangularising a matrix by a series of plane rotations is known as QR decomposition, Q being a matrix of rotation parameters and R the triangular matrix. Triangular array processing functions for implementing rotation algorithms are well known in the prior art, such as the international application referred to above, and will not be described further.

The rotation parameters pass along rows of cells such as uppermost row $B_{11}$ to $I_{1r}$. They thereafter pass into a rectangular array 58 of internal cells $I_{1,r+1}$ to $I_{r-1}$ and multiplier cells $M_{r+1,r+1}$ to $M_{r+1,r+d+1}$ indicated by hexagons. The boundary cells $B_{11}$ to $B_{rr}$ have the additional function of cumulatively multiplying their cosine rotation parameters (or cosine-like parameters in other algorithms). For example, when the first boundary cell $B_{11}$ generates sine and cosine parameters on a clock cycle and outputs them to internal cell $I_{12}$ to the right, it also outputs the cosine parameter diagonally below and to the right to the second row, second column boundary cell (not shown, would be designated $B_{22}$). This cell multiplies by its cosine parameter generated two cycles later, there being a two clock cycle delay between a diagonal output from one boundary cell and a like output from its diagonal neighbour incorporating the first such cell's output. This diagonal boundary cell function generates products arising from cumulatively multiplied cosine parameters, each product generated from a respective input row of the matrix output from the digital arithmetic unit 52. Each product is fed to the row of multiplier cells $M_{r+1}$ to $M_{r+1,r+d+1}$, and passes along it at the rate of one multiplier cell per clock cycle. Similarly, rotation parameters passing along rows of the triangular array 54 are fed into respective rows of the rectangular array 58. These parameters are employed by the rectangular array's internal cells $I_{1,r+1}$ etc to rotate data received from above, to update respective stored elements, provide output below and pass the parameters to the right; i.e. the rectangular array's internal cells operate in precisely the same way as those of the triangular array 54.

The multiplier cells (referred to generally as M) have the processing function of receiving data from above, multiplying it by an input from the left, outputting the product below and passing on to the right the left hand input. The product is the scalar least squares residual error obtained in fitting the transformed data from the arithmetic unit 52 to data passing down the column surmounting the relevant multiplier cell in each case. Sets of residuals output by the rectangular array 58 form respective least squares residual vectors.

The rectangular array 58 is notionally partitioned into a multi-column portion 58a and a single column portion 58b.

The triangular array 54 and the rectangular array 58 receive different input data. The former receives data from the input DI which has undergone transformation in the digital arithmetic unit 52, as has been said. The rectangular array receives input data from the answer input AI via chains of latches (not illustrated explicitly). These are indicated as an L-shaped delay device 60 incorporated in the heuristic process 44; the device 60 is notionally partitioned into a multichannel portion 60a and a single channel portion 60b connected respectively to portions 58a and 58b of the rectangular array 58.

The data input bus DI is connected to the arithmetic unit 52 via a temporal skewing device indicated by a triangle 62. This device is a triangular array of clocked latches (not shown). It introduces a time delay which varies in magnitude across the input bus DI. The delay is zero at the upper edge of the input bus DI, and increases by one clock interval $\tau$ per bus segment (not illustrated) to $(d-1)\tau$ at the lower edge of the bus. Similarly, a second temporal skewing device 64 introduces a like skew delay variation at 64a in the answer input bus AI together with a delay of $d\tau$ at 64b in the subsidiary answer input bus SAI. Output from the rectangular array 58 passes via a temporal deskewing device 66 similar to the device 62. The former introduces a rectangular array output delay varying from $d\tau$ for the column of cells $I_{1,r+1}$ to $M_{r+1,r+1}$ to zero at the rightmost column of cells $I_{1,r+d+1}$ to $M_{r+1,r+d+1}$. The delay reduces by one clock cycle interval $\tau$ per column.

The purpose of the input delay devices 62 and 64 is to ensure correct timing of arrival of data within the heuristic processor elements 52, 54, 58a and 58b irrespective of data path. The deskewing delay device 66 provides for data input synchronously at DI, AI and SAI to give rise to synchronous outputs at an output interface indicated by a line 68. The line 68 has portions 68a and 68b corresponding to outputs from rectangular array portions 58a and 58b respectively. The use of triangular arrays of clocked latches such as 62, 64 and 66 is well known in the art of systolic array processing and will not be described further.

The heuristic processor 44 has two alternative modes of operation selectable by a signal applied to an input Tr/Te. A high (binary 1) signal implements Tr (training) mode, and a low (binary 0) signal implements Te (test) mode. This mode selection signal is passed on to triangular and rectangular arrays 54 and 58 via an appropriate delay (not shown) within the arithmetic unit 52 and via a connection 70.

In the training mode, training data is derived from the nonlinear system 14 via the computer 22 and FIR filter 30 as previously described, and is fed to the data input bus DI after delay at 46. The undelayed version of the training data is fed to the answer input AI, the switch 42 being set to connect buses 40a and AI together. The delayed data undergoes a transformation in the digital arithmetic unit 52. This involves computation of the Euclidean norm (geometrical distance) of each data vector from each of a set of centres (geometrical origins). Here each data vector is a respective set of phase space coordinates. Each such norm then undergoes a nonlinear transformation. The results of the transformation then undergo QR decomposition in the triangular array 54. This provides rotation parameters for application to undelayed data (leading by p clock cycles) in the rectangular array 58 received via the delay device 60. In the training mode, the boundary and internal cells $B_{11}$ to $I_{r,r+d+1}$ all operate adaptively; i.e. in generating and applying rotation parameters respectively they update their stored matrix elements on every clock cycle in accordance with each new set of inputs.

The result of operation in the training mode is that data delayed by p clock cycles (interval $p\tau$) becomes transformed and least squares fitted to undelayed data. The accuracy of the fit is indicated by residual values (errors) appearing at the heuristic processor output 68. An acceptably accurate fit is indicated by small fluctuating residual values.

At the end of training, the boundary and internal cells $B_{11}$ to $I_{r,r+d+1}$ have respective matrix elements stored therein. In the first (multicolumn) rectangular array portion 58a, the elements map a point having co-ordinates $g_k(i)$ (k=1 to d) on a trajectory in a d-dimensional phase space on to a point p steps later on that trajectory and having co-ordinates $g_k(i+p)$. In the second (single column) rectangular array portion 58b, the matrix elements map the point $g_k(i)$ (k=1 to d) on to a digitised time series value $V(t_{i+n-1+p})$ also p steps ahead.

When training is complete, the mode control input Tr/Te is set to a low voltage signal level (binary 0) to implement test mode. This is relayed to the triangular and rectangular arrays 54 and 58 via the connection 70. It switches all the boundary and internal cells of the kinds B and I in these arrays into modes where internal matrix element update is suppressed. Evaluation and application of rotation parameters in the cells B and I respectively continues however. In consequence, the mathematical model expressed by stored matrix elements derived during training is frozen.

There are two alternative test modes of operation depending on the setting of the switch 42. In both modes, the "known" or "comparison" nonlinear system 14 is replaced by an "unknown" nonlinear system required to be compared with the former. The first mode involves the switch 42 remaining in the training setting, and thereby connecting bus spur 40a to answer input AI. Data derived from the unknown system is then transformed into co-ordinates $g_k'(i)$ etc by the FIR filter 34 employing singular vectors $f_1$ to $f_d$ derived from the known system 14.

The co-ordinates $g_k'(i)$ etc are fed directly to the answer input AI because of the setting of the switch 42. They are also fed via the delay 46 to the data input DI. The associated time series values $V'(t_i)$ are fed to the subsidiary answer input SAI. The input at DI becomes transformed nonlinearly into an r-dimensional space by the arithmetic unit 52. The output from the unit 52 is further transformed by the frozen mathematical model stored in the triangular and rectangular arrays 54 and 58. After this further transformation it is substracted in the rectangular array 58 from co-ordinates and time series values received from the delay device 60. This gives rise to error values at the processor output 68. Each error value is the difference between a respective measured value from the unknown nonlinear system and an associated predicted value calculated by the heuristic processor 44 from its frozen mathematical model. If the error values are sufficiently small the unknown non-linear system is demonstrated to be equivalent to the known system 14, in that its future behavior is predictable p steps ahead on the basis of the behavior of the known system. This predictability will occur in both phase space (rectangular array portion 58a) and in the corresponding time series (rectangular array portion 58b). This is a demonstration that signals from a trial system can be used to detect and quantify their similarity to those from a previously observed "standard" system.

This first test mode of operation is also important for the purpose of detecting changes in the operation of systems which may be chaotic but are deterministic in the mathematical sense. For example, an oscillatory system such as a rumbling mechanical bearing may affect readings from a transducer arranged to monitor a parameter of the device of which the bearing is part. In this case, the "known" nonlinear system 14 used in training will be the device with the bearing in good working order. The transducer output (which contains bearing rumble) is also the "unknown" system. The "error values" output at 68 during test mode will be small so long as the bearing operates normally. The error values will increase as the bearing degenerates through wear. This is a demonstration that signals from systems are separable in accordance with the invention when they become dissimilar.

The second test mode of operation requires the switch 42 to be set to its second position. This disconnects the bus spur 40a and applies a binary zero signal level to each segment of the answer input AI. In other respects, operation in the second test mode is as in the first. In consequence, data input at DI and transformed at 52, 54 and 58 becomes compared to zero signals input to the rectangular array 58 from the delay device 60. In consequence, the error values appearing at the output interface 68 are in fact generated from comparisons with zero signals. These values are therefore estimates of the co-ordinates in phase space (output 68a) and the time series (output 68b) of the "unknown" system p steps (clock cycles) in the future in each case. The predictions are made on the basis of the multidimensional matrix model built up during training of the triangular and rectangular arrays 54 and 58 and stored therein. This demonstrates that the prediction device 10 has the capacity for generating predictions of future states of a nonlinear dynamical system.

The mode of operation of the computer 22 will now be described in more detail. The computer 22 is programmed to carry out a sequence of operations; this produces a singular value decomposition of the time series data of the kind $V(t_i)$ from the "known" system 14. The sequence is as follows:

(a) Determine an acceptable value for n, the number of dimensions in phase space;

(b) Carry out a singular value decomposition of time series $V(t_i)$ etc to define a basis for the phase space;

(c) Determine noise-corrupted singular functions generated in (b) and omit them to produce a d-dimensional sub-space;

(d) Load singular vectors into FIR filter 34;

(e) Activate FIR filter 34 by clock signal to read in $V(t_i)$ etc; and (f) Activate heuristic processor 44 n clock cycles after (e) to start input of co-ordinates and signals of the kind $g_k(i)$ and $V(t_i)$.

To carry out the above operations, the computer 22 reads in the digitised time series having the general term $V(t_i)$, where i=1 to M. A typical value for M would be 50,000. It converts the terms in the time series to a set of normalized values by calculating their statistical mean and variance, subtracting the mean from each term and dividing the result by the variance. For convenience, a normalized time series value derived from and equivalent to a sampled ADC output signal $V(t_i)$ will also be referred to below as $V(t_i)$.

For test purposes, a "known" nonlinear system 14 was constructed. This consisted of a mechanical bearing in the form of a ball race, an aluminium bar contacting the center of the race, and a positional transducer contacting the bar. The transducer was a piezoelectric crystal pickup of the kind used to contact records in domestic record players. It gave an electrical output indicating bearing rumble, i.e. unwanted and at least partly deterministic nonlinear bearing vibration.

Figure 2:
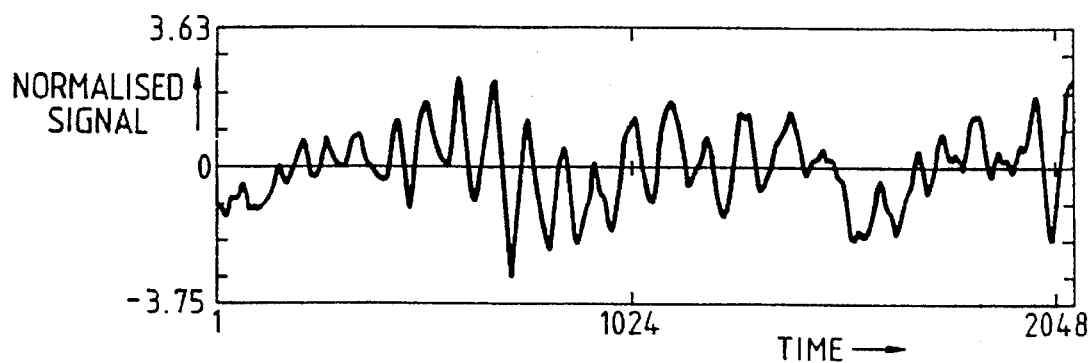
FIG. 2 is a graph of a time series of signals for input to the FIG. 1(a) device.

The transducer produced a time series of 50,000 (i.e. M) values. The first 2048 of these are shown in FIG. 2 in digitised form after normalization by the computer 22.

To carry out operation (a) (as defined above) and determine an acceptable number n of phase space dimensions, the computer 22 calculates the autocorrelation function of the (now normalized) time series $V(t_i)$ etc. Writing $V_i$ for $V(t_i)$, the general term of the normalized time series, in order to reduce complexity of equations, the autocorrelation function G has successive values of the kind $G_k$ defined by:

$$G_k = (M-K)^{-1} \sum_{i=1}^{M-K} V_i V_{i+k} \qquad (4)$$

where k=0, 1, 2, 3, ... (K−1), where K is the maximum value of k, and K is less than M.

Figure 3:
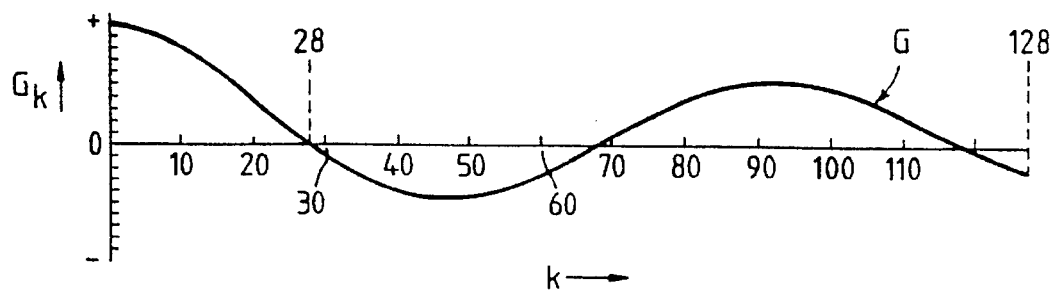
FIG. 3 is a graph of an autocorrelation function of the FIG. 2 time series.

FIG. 3 shows the autocorrelation function G for the normalized time series data shown in FIG. 2. The computer 22 calculated the function G over values of k from 1 to 128, and the values $G_k$ are shown plotted in arbitrary units against k in FIG. 3.

The autocorrelation function G crosses the k axis, i.e. $G_k$=0, at approximately k=28. It has been found empirically that an appropriate value of n, the number of phase space dimensions, is equal to the first value of k at which $G_k$=0. The value of n is therefore chosen to be 28.

The computer 22 now implements operation (b), the singular value decomposition of the time series. To do this, it forms a matrix X in which successive rows are successive Takens' vectors $T_i$ etc. The latter are defined by $$T_i = [V_i, V_{i+1}, \ldots V_{i+n-1}] \quad (5)$$

Equation (5) shows that the ith Takens' vector $T_i$ (i=1 to M−n+1) has vector elements which are a sequence of n successive time series values beginning with $V_i$. This is discussed by F Takens in "Detecting Strange Attractors in Turbulence", Lecture Notes in Mathematics, Ed. D. A. Rand and L. -S. Young, Springer, Berlin, 1981 p. 366. X is therefore given by:

$$X = \begin{bmatrix} T_1 \\ T_2 \\ \cdot \\ \cdot \\ \cdot \\ T_{M-n+1} \end{bmatrix} = \begin{bmatrix} V_1 & V_2 & \ldots & V_n \\ V_2 & V_3 & \ldots & V_{n+1} \\ \cdot & & & \cdot \\ \cdot & & & \cdot \\ \cdot & & & \cdot \\ V_{M-n+1} & & \ldots & V_M \end{bmatrix} \quad (6)$$

The transpose of X is $X^T$ given by:

$$X^T = [T_1^T \ldots T_{M-n+1}^T] \quad (7)$$

$$\text{ie } X^T = \begin{bmatrix} V_1 & V_2 & \ldots & V_{M-n+1} \\ \cdot & \cdot & & \cdot \\ \cdot & \cdot & & \cdot \\ \cdot & \cdot & & \cdot \\ V_n & V_{n+1} & & V_M \end{bmatrix} \quad (8)$$

The autocovariance matrix $\Xi$ is defined by:

$$\Xi = X^T X \quad (9)$$

$\Xi$ is then processed by the computer 22 to provide the required singular value decomposition. This matrix is subjected to the well known mathematical process of diagonalisation. The process consists of Householder transformation of the matrix to tri-diagonal form, followed by application of the QR algorithm to provide eigenvalues. The eigenvalues are the squares of the required singular values. This is described by W H Press et al. in "Numerical Recipes—The Art of Scientific Computing", Cabridge, p. 350 et sequi. Also, the decomposition yields a set of n (in the present example n=28) singular vectors expressed as sets of digital values defining mathematical functions $f_1$ to $f_n$. Each singular vector is associated with a respective singular value $s_1$ to $s_n$, which might loosely be referred to as the strength of the respective vector. The decomposition may be thought of as generating the higher dimensional equivalent of an ellipsoid having axes directed as indicated by respective singular vectors and axial lengths given by respective singular values. This is discussed by W H Press et al (as referred to above) at pages 52 to 64.

The lengths or strengths of the singular vectors, i.e. their respective singular values, are arranged to reduce monotonically as j increases, where j is the vector index number in $f_j$ and j=1 to n. It will normally fall to the nonlinear system's noise level before j reaches n. This indicates that singular vectors associated with singular values which are small are significantly corrupted by noise. Such vectors should therefore be omitted. Consequently, the dimensionality of the phase space reduced from n to d, where singular values $s_1$ to $s_d$ are greater in magnitude than the noise level.

In a correctly designed analyser 10, the ADC 16 would be arranged to render the noise level approximately equal to but greater than the least significant bit of the ADC's output digital word.

The programming of a computer to deal with equations (4) to (9), to truncate the singular value decomposition and to supply appropriately timed data and clock signals is straightforward and will not be described. Singular value decomposition in the foregoing context is described by Broomhead et al in Physica 20D, 1986, p. 217.

Figure 4A:
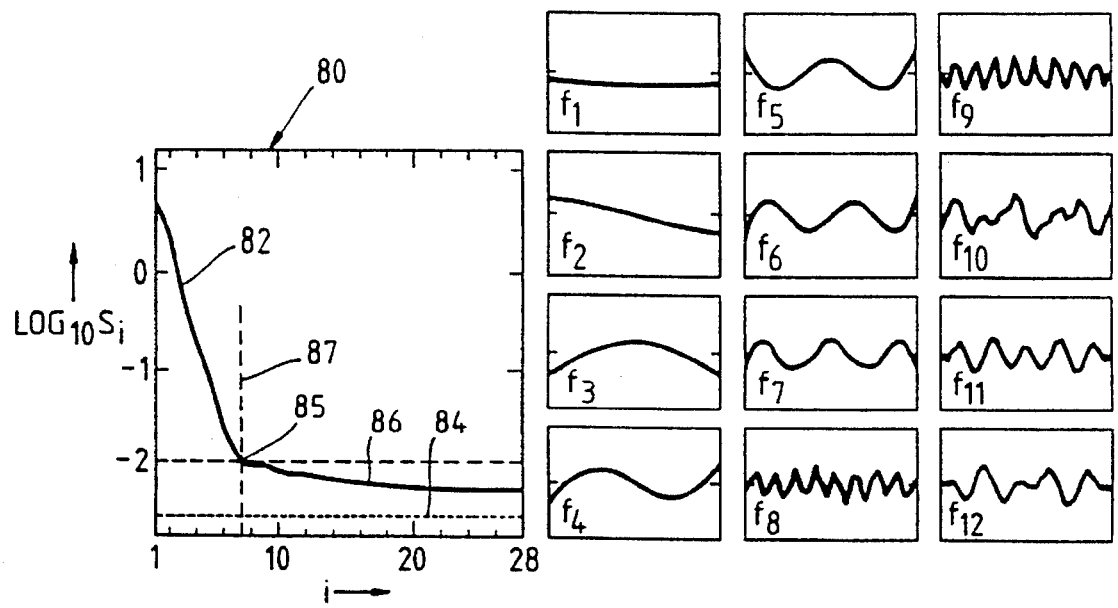
FIGS. 4(a) and 4(b) provide the results of a singular value decomposition of the FIG. 2 time series and indicates a system noise level above digital quantization noise.
Figure 4B:
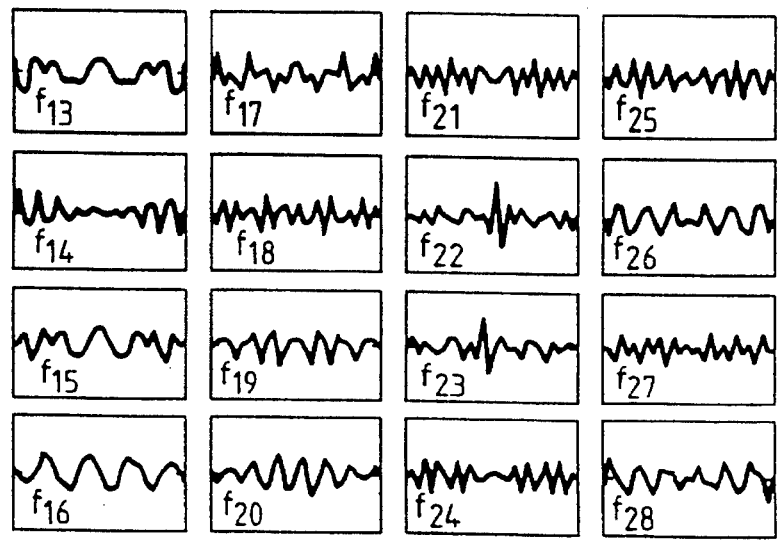

Referring now to FIGS. 4(a) and 4(b), there are shown the results of a singular value decomposition of the 50,000 normalized digital time series values obtained from the ball race bearing referred to earlier. A plot indicated generally by 80 provides the spectrum of the singular values $s_1$ to $s_n$ produced in the decomposition. In the present example n=28, so the values are $s_1$ to $s_{28}$ with a general value $s_i$ say, in which i=1 to 28. The plot 80 shows a monotonically falling curve 82 of $\log_{10} s_i$ against singular value (or singular vector) number i from 1 to 28. At i=1, the curve 82 has a logarithm of 0.6 approximately, corresponding to a relative magnitude of about 4. At i=28, it also falls to a logarithmic value of about −2.3, equivalent to about $5 \times 10^{-3}$. It does not cross the noise level of the ADC 16 (indicated by a chain line 84). However, as indicated at a point 85 where horizontal and vertical chain lines 86 and 87, an elbow appears in the curve 82. To the left of the vertical line 87, the curve 82 varies rapidly with singular value number i; to the right of this line, the variation of $\log_{10} s_i$ with i is insignificant. The vertical line 87 is at i=7. For i equal to 8 or more, it can be inferred that the nineteen singular values are corrupted by noise arising in the system 14 and sensor transducer 12. This inference can be taken because noise is homogeneously distributed, and lack of variation in a spectrum is normally associated with a noise level. The horizontal chain line 86 is consequently treated as the system noise level (as opposed to the ADC quantisation noise level 84). Singular vectors for which i>7 are therefore considered to be unacceptably corrupted by noise. Singular vectors or functions $f_1$ to $f_7$ have an acceptable degree of noise. These are consequently retained, and $f_8$ to $f_{28}$ are discarded. This creates a noise-reduced subspace of the nonlinear system, which subspace in the present example has seven dimensions. The value of the parameter d in equation (2.d) is therefore 7.

FIGS. 4(a) and 4(b) show the twenty-eight singular vectors generated by singular value decomposition in the present example, the vectors being shown as curves labelled $f_1$ to $f_{28}$.

To compare FIGS. 4(a) and 4(b) with classical Fourier analysis, it is noted that the latter assumes infinitely long (and therefore impractical) time series. Fourier analysis characterises linear systems with discrete frequencies (line spectra). It is not useful for nonlinear systems which exhibit broad band spectra.

If required, it is possible to combine the alternatives provided by the switch 42 in FIG. 1(a). This requires the switch 42 to be removed and a third portion 58 (not shown) to be added to the rectangular array 58. The portion 58c would be of like construction to portions 58a and 58b combined. In training mode, the portion 58c would receive input from AI, which would be bifurcated for this purpose. In test mode the portion 58c would receive zero inputs. A third output (say 68c) would then provide predicted values of co-ordinates and time series while errors between these values and measured parameters would appear at 68a and 68b.

Referring now to FIGS. 5(a) and 5(b), there are shown results similar to those shown in FIGS. 4(a) and 4(b) but obtained from a modified Van der Pol electronic oscillator. Such an oscillator has very small inherent noise. Any noise which appears in the course of signal processing is due to ADC quantisation. FIGS. 5(a) and 5(b) show a singular value spectrum 90 falling below an estimate of an ADC quantization level 91 at i=13 approximately. The level 91 is the standard deviation of the relevant time series divided by one in the associated ADC's least significant bit channel. The spectrum 90 levels out at about i=20. ADC quantization noise therefore dominates the results, and the spectrum requires truncation at i=13 (giving d=13). With a more sensitive ADC 16, truncation could be extended to i=20.

FIGS. 5(a) and 5(b) also show the forms of the singular vectors or functions obtained in singular value decomposition. There are thirty-eight, i.e. i=1 to 38.

Referring now to FIG. 6, there is shown a functional block diagram of part of a further embodiment 110 of the invention. It is a dynamical system analyzer which is a modification of that shown in FIG. 1, and parts equivalent to those described earlier have like references. In the case of numerical references, 100 has been added to each.

In view of the similarities between the analyzers 10 and 110, the description of the latter will concentrate on aspects of difference.

The analyzer 110 has an heuristic processor 144 and FIR filter 134 equivalent to those previously described. The FIR filter 134 is illustrated laterally inverted such that its latch chain 136 appears on the right. The latch chain 136 is extended by three additional latches $136_{n+1}$, $136_{n+2}$ and $136_{n+3}$ as compared to latch chain 36. The latches $136_n$ to $136_{n+3}$ are connected to respective inputs $SAI_0$ to $SAI_3$ collectively forming a subsidiary answer input SAI. The inputs $SAI_1$, $SAI_2$ and $SAI_3$ are connected via respective input delay units $115_1$ to $115_3$ to a delay device 160 incorporated in the heuristic processor 144. There is no equivalent of the switch 42. The input delay units $115_1$, $115_2$ and $115_3$ implement respective delays of $\tau$, $2\tau$ and $3\tau$, where $\tau$ is a clock cycle as before.

Signals pass from the delay device 160 into respective columns $C_0$ to $C_3$ forming in combination an output array 158b. The array 158b is equivalent to a multi-column version of the column 58b of the earlier embodiment, in which least squares fitting to normalized time series data was implemented. The columns $C_0$, $C_1$ and $C_2$ are in series with output delay units $117_0$, $117_1$ and $117_2$ respectively; the latter provide delays of $3\tau$, $2\tau$ and $\tau$ respectively, and in consequence signals reaching an output interface 168 are temporally deskewed (as compared to the equivalent output from columns $C_0$ to $C_3$).

The system analyzer 110 operates as follows. A training procedure is employed equivalent to that described earlier. A comparison system (not shown) provides a time series of signals from which singular vectors $f_1$ to $f_d$ are derived by singular value decomposition and truncation. The vectors are loaded into the FIR filter 134, and the time series $V_1 \ldots V_i \ldots$ is clocked along the latch chain 136. In training mode, phase space coordinates output from the FIR filter 134 become nonlinearly transformed, QR decomposed and fitted to time series data as described for the earlier embodiment 10. However, in the present embodiment, instead of a single number (p) of clock cycle delays in the device 46, there are four independent delays of 0, 1, 2 and 3 clock cycles (intervals $\tau$). To implement this, the delay circuitry has been rearranged somewhat, making use of the latch chain 136 and adjusting for delays experienced by rotation parameters passing between successive columns $C_0$ to $C_3$. The input delay units $115_1$ etc provide that adjustment.

In consequence, during training the ith set of phase space coordinates $g_1(i)$ to $g_d(i)$ output from the FIR filter 134 becomes associated by the heuristic processor 144 with each of the following time series points: $V_{i+n-1}$, $V_{i+n}$, $V_{i+n+1}$ and $V_{i+n+2}$. This is carried out in respective columns $C_0$ to $C_3$; i.e. column $C_{q+1}$ is responsible for fitting the transformed version of $g_1(i)$ to $g_d(i)$ to $V_{i+n+q}$, where q is $-1, 0, 1$ or 2 and q is equivalent to p–1.

The columns $C_0$ to $C_3$ provide error values between transformed versions of $g_1(i)$ to $g_d(i)$ and $V_{i+n-1}$, $V_{i+n}$, $V_{i+n+1}$ and $V_{i+n+2}$. The prediction interval increases from 0 to 3 clock cycles between columns $C_0$ to $C_3$, and consequently the disconformity or error is likely to increase also.

FIG. 7 is an indication of what might be expected as an output from an analyzer similar to the analyzer 110 but having eleven output columns $C_0$ to $C_{10}$ (not shown). It is a plot 200 of the logarithm to base 10 of the RMS prediction error against prediction interval, the latter being the number p of clock cycle intervals ($\tau$); here p goes from 0 to 10, and is the suffix of the respective output column $C_0$, $C_1$, $C_2 \ldots C_{10}$ in each case. A graph such as the graph 200 may be employed to identify the degree of predictability of a nonlinear dynamical system. The RMS prediction error shown in FIG. 7 is seen to increase with increasing p up to some maximum level at which it saturates. The saturation level is caused by the fact that even if the analyzer made the worst guess possible the prediction error will be limited to some maximum, determined by the training and processing 'attractor sizes'.

The result shown in FIG. 7 is calculated as follows. The sequence of values $x_t$, t=0 to 4000 are generated by iterating the difference equation $$x_t = 1 - \alpha(x_{t-1})^2 + \beta x_{t-2} \tag{10}$$

The parameters $\alpha$ and $\beta$ are constants with values $\alpha=1.4$, $\beta=0.3$. These values are chosen so that the sequence is chaotic, and a small starting value is used for $x_0$. The sequence of values of $x_t$, where t=1001 to 2000, are used to train the dynamical system analyzer using 36 centers uniformly distributed across a plane bounded by the points (2, 2), (2, -2), (-2, -2) and (-2, 2). The sequence of values of $x_t$, where t=3001 to 4000, are then processed, and $\text{Log}_{10}$ of the RMS prediction error is calculated using the respective set of 1000 error values which appear from each of the output columns $C_0$ to $C_{10}$.

The invention may be implemented in an alternative manner to that previously described. The analyzer 10 for example was operated in successive training and test modes. It is however possible for a training procedure on one analyzer to produce results employed by a different device. Referring to FIGS. 1 and 1a once more, the training procedure in the heuristic processor 44 generates a set of matrix elements. The matrix element values become finalized when training is ended, and they are stored on individual internal and boundary cells I and B. In test mode, these values are frozen, and they implement a mathematical (matrix) transformation on data output from the digital arithmetic unit 52, which itself implements a nonlinear expansion about a set of centres. The matrix transformation is equivalent to multiplication by a weight vector or weight matrix; individual elements of the weight vector or matrix are obtainable from the trained heuristic processor. The procedure is set out in PCT App. No. PCT/GB90/00142 previously cited, and will not be described in detail. However, having such weighting elements and singular vectors determined in a training procedure, together with the centres and nonlinear transformation (unit 52) used in training, operation in test mode may be by means of a simple weighting device operating on the output of the digital arithmetic unit 52. This enables the apparatus requirements of test devices to be reduced.

It has been found that the invention might, in certain circumstances, prove to be too sensitive to minor departures of a dynamical system from expected behaviour. In other words a small departure might give a large error. In this case it is possible to employ the invention in a different manner, as will now be described.

As has been said, the heuristic processor 44 operating in training mode builds up stored elements which are related to a weight matrix. Elements of the weight matrix may be obtained at the output 68 by input of unit vectors to the triangular systolic array 54 as described in PCT/GB90/00142. This enables a dynamical system to be characterised by the elements of the weight matrix to which it gives rise in the heuristic processor 44. Data from a comparison dynamical system may therefore be input to an analyser of the invention and employed therein to generate weight matrix elements for subsequent read out. These elements are then available for comparison with weight matrix elements of any trial system. If the weight matrices of the comparison system and the trial system are similar, then the two systems are alike.

It is not in fact essential to convert elements stored on internal and boundary cells I and B to weight matrices in order to compare the trial and comparison systems. Since each set of stored elements is directly related to a weight matrix, and the relationship is invariant, stored elements from the trial and comparison systems may be compared with one another directly without intervening transformation to weight matrices.

There are two approaches to obtaining the weight matrix of the trial system. One approach is to retrain the analyzer 10 using data from the trial system; i.e. after the analyzer 10 has been trained using comparison system data, the comparison system weight matrix is read out and the whole training procedure previously described is carried out once more. The computer 20 consequently carries out a singular value decomposition of data derived from the trial system, and it loads the FIR filter 34 with singular vectors derived in that decomposition. The heuristic processor 44 subsequently processes the output of the FIR filter 34 as previously described to build up elements stored on internal and boundary cells.

The second approach is for the heuristic process 44 to operate as previously described for the training mode, but the FIR filter 34 is loaded with singular functions derived from the singular value decomposition of data from the comparison system. There is no such decomposition of trial system data. In consequence, the trial system data is transformed to phase space coordinates using comparison system singular functions. Subsequently, the phase space coordinates so produced undergo processing in the heuristic processor as previously described to build up a trial system set of stored elements related to a weight matrix.

We claim:

1. A dynamical system analyser including:
   (1) means for generating a sequence of sets of phase space coordinates from a time series of signals from a dynamical system, each coordinate set being projections of a respective Taken' vector derived from signals from the time series on to a set of singular vectors obtained in a singular value decomposition of said time series of signals, and
   (2) heuristic processing means for transforming said sequence to produce a fit to reference data and to create a mathematic model related to that transformation.

2. A dynamical system analyser according to claim 1, wherein said means for generating comprises:
   means for deriving a time series of signals from a dynamical system;
   means for generating from the time series a set of singular vectors each vector associated with a respective singular value which is greater than a noise level of the dynamical system, said set defining a phase space and corresponding to a subset of a singular value decomposition of the time series; and
   means for transforming the time series into a sequence of sets of phase space co-ordinates by projecting respective Taken's vector of signals from the time series on to the set of singular vectors.

3. A dynamical system analyser according to claim 1, wherein said heuristic processing means includes a means, operating in a training mode, for carrying out QR decomposition and a least squares fitting to said reference data in order to generate said mathematical model.

\* \* \* \* \*

UNITED STATES PATENT AND TRADEMARK OFFICE
CERTIFICATE OF CORRECTION

PATENT NO. : 5,493,516
DATED : February 20, 1996
INVENTOR(S) : BROOMHEAD et al.

It is certified that error appears in the above-identified patent and that said letters patent is hereby corrected as shown below:

In the Abstract, line 17, change "transforation" to --transformation--.

Column 16, line 15, change "Taken'" to --Takens'--; and line 37, change "Taken's" to --Takens'--.

Signed and Sealed this

Fourth Day of February, 1997

Attest:

BRUCE LEHMAN

Attesting Officer      Commissioner of Patents and Trademarks